United States Patent [19]
Kroll et al.

[11] Patent Number: 5,782,883
[45] Date of Patent: Jul. 21, 1998

[54] SUBOPTIMAL OUTPUT DEVICE TO MANAGE CARDIAC TACHYARRHYTHMIAS

[75] Inventors: Kai Kroll; Mark W. Kroll, both of Minnetonka, Minn.

[73] Assignee: Galvani Ltd., Minneapolis, Minn.

[21] Appl. No.: 548,013

[22] Filed: Oct. 25, 1995

Related U.S. Application Data

[63] Continuation-in-part of Ser. No. 251,349, May 31, 1994, abandoned.
[51] Int. Cl.$^6$ ................................................. N61N 1/39
[52] U.S. Cl. ................................................. 607/14
[58] Field of Search .............................. 607/4, 5, 6, 9, 607/10, 14, 22, 23

[56] References Cited

U.S. PATENT DOCUMENTS

| | | |
|---|---|---|
| 3,638,656 | 2/1972 | Grandjean et al. |
| 4,222,386 | 9/1980 | Smolnikov et al. |
| 4,349,030 | 9/1982 | Belgard et al. |
| 4,945,909 | 8/1990 | Fearnot et al. |
| 4,996,984 | 3/1991 | Sweeney et al. |
| 5,018,522 | 5/1991 | Mehra et al. |
| 5,042,497 | 8/1991 | Shapland et al. |

FOREIGN PATENT DOCUMENTS

| | | |
|---|---|---|
| 9306886 | 4/1993 | European Pat. Off. |
| 540266 | 5/1993 | European Pat. Off. |
| 9319809 | 10/1993 | European Pat. Off. |

OTHER PUBLICATIONS

Kirchhof, et al. * "Regional Entrainment of Atrial Fibrillation Studied by High Resolution Mapping in Open–Chest Dogs." Circulation 1993; 88: 736–749.

Ken Knight, et al.* "Regional Capture of Fibrillating Right Ventricular Myocardium: Evidence of an Excitable Gap in VF Using High Resolution Cardiac Mapping." J. Am. Coll Card 1994; 283A.

Schuder, et al.* "Transthoracic Ventricular Defibrillation in Dogs With Unidirectional Rectangular Double Pulses." Cardiovasc Res. 1970; 4: 497–501.

Kugelberg, et al.* "Ventricular Defibrillation with Double Square Pulses."Med & Biol Eng., 1968; 6: 167–169.

Kugelberg, et al.* "Ventricular Defibrillation: A New Aspect." Acta Chirurgica Scandinavia 1967: Supplement 372.

Resnekov* "Ventircular Defibrillation by Monophare Trapezoidal shaped Double–pulses of Low Electrical Energy." Cardiovasc Res. 1968; 2: 261–264.

Geddes, et al.* "Ventricular Defibrillation with Single and Twin Pulses of Half–Sinusoidal Current." J Applied Physiology, 1973; 34: 8–11.

*Primary Examiner*—William E. Kamm
*Attorney, Agent, or Firm*—Patterson & Keough, PA

[57] ABSTRACT

An implantable device for, in the event of ventricular fibrillation, temporarily electrically forcing cardiac output to maintain life and consciousness in a patient until the patient is rescued by an external defibrillator. The device uses moderate voltage output pulses of 30–200 V which are sufficient to cause a partial contraction of the heart even if it is fibrillating. These pulses are not typically sufficient to defibrillate the heart and this device cannot substitute as a defibrillator. However, the moderate voltage pulsing will generate enough cardiac output to keep the patient alive. The system is designed with sufficient battery power for years of monitoring and hours of cardiac output forcing operation.

23 Claims, 12 Drawing Sheets

HIGH COMFORT PULSE

HIGH EFFICIENCY PULSE

SUBOPTIMAL OUTPUT DEVICE TO MANAGE CARDIAC TACHYARRHYTHMIAS

RELATED APPLICATIONS

This application is a continuation-in-part of Ser. No. 08/251,349 filed on 31 May, 1994 entitled, "Method and Apparatus For Temporarily Electrically Forcing Cardiac Output in a Tachyarrhythmia Patient" which application is now abandoned.

FIELD OF THE INVENTION

The present invention generally relates to the field of therapies for cardiac arrhythmias. Specifically, the invention pertains to a method and apparatus for forcing cardiac output to control and manage cardiac arrhythmias by stimulating fibrillating cardiac cells to affect a partial contraction of the heart. The pulses are conditionally tailored, to yield a level of voltage at a specified rate and duration, to treat a prevailing arrhythmic condition. More specifically, the invention pertains to a method and apparatus for electrically forcing cardiac output by delivering a series of pulsed electrical fields to the heart. The pulsed electrical fields are tailored to stimulate cardiac cells to control ventricular fibrillation, hemodynamically compromising tachycardia, and/or ventricular tachycardia.

BACKGROUND OF THE INVENTION

Atrial fibrillation is a common occurrence in cardiac patients. It is generally caused by the lack of blood output from the atria and usually leads to blood clots in the atria. The blood clots may lodge in either the lungs or the brain resulting in serious health problems, strokes or possibly death to the patient.

Various types of oral drugs have been tried to treat atrial fibrillation. While some patients are helped by these drug therapies, the majority of patients are not successfully and safely treated and require a different type of treatment. One of the most significant shortcomings of these drugs is the side effects they may have on the patients. Specifically, in some patients, the administration of these drugs leads to a ventricular fibrillation which may be immediately fatal.

Traditional prior art provides a number of devices and methods to control atrial fibrillation. Generally, the prior art discloses defibrillation systems which utilize electrical shock therapy. For example, U.S. Pat. No. 4,572,191 and U.S. Pat. No. 3,952,750 disclose shock therapy devices. Further, recently issued U.S. Pat. No. 5,282,837, U.S. Pat. No. 5,265,600 and U.S. Pat. No. 5,391,185 disclose various embodiments relating to implantable electrical atrial defibrillators.

The use of electrical shock to treat atrial defibrillation poses some hitherto unresolved problems. Primarily, electrical atrial defibrillation requires shocks in the order of one or two joules of electrical energy. This shock magnitude is very painful to the patient and is therefore undesirable. More importantly, another disadvantage of electrical shock therapy is the fact that it may lead to ventricular fibrillation. This is because a moderate level shock during repolarization of the ventricles will typically result in fibrillation. In order to avoid this problem, the prior art utilizes methods and apparatus to sense the R-wave in the right ventricle and carefully synchronizes the atrial shock to avoid impinging upon the ventricular T-wave which would represent the repolarization of the ventricle. The risk of fibrillating the heart with an atrial defibrillation shock can also be minimized by delivering shocks which are timed with ventricular activity. This method is generally disclosed in U.S. Pat. No. 5,207,219; U.S. Pat. No. 5,282,837 and U.S. Pat. No. 5,350,402.

In spite of the advances made by the prior art, atrial defibrillation shock therapy may cause ventricular fibrillation and therefore a therapy for an otherwise non-fatal condition might prove fatal to the patient. As is disclosed hereinbelow, one aspect of the present invention provides a practical method and device to safely treat ventricular fibrillation which may result from atrial defibrillation shock therapy and/or occur in conjunction with other cardiac problems.

Traditional prior art does not provide a life sustaining device for use in emergency situations involving hemodynamically compromising ventricular tachycardia and ventricular fibrillation. High risk patients may need some cardiac output as part of a set of therapies to maintain life.

Approximately 400,000 Americans succumb to ventricular fibrillation each year. As indicated hereinabove, ventricular fibrillation could be fatal and may only be terminated by the application of an electrical shock delivered to the heart. This is typically done using electrodes to apply the shock to the heart. The voltage in such a shock is usually in the range of 1,000–5,000 volts. Although this shock is sufficient to defibrillate the heart and restore normal rhythm, a prompt and timely response is required to achieve this objective. Moreover, a delayed response would result in a permanent cardiac damage or death to the patient. Experience has shown that paramedics cannot respond rapidly enough to restore life in emergency situations of patients needing defibrillation shock therapy. For example, in New York City nearly 99% of cardiac arrest patients die because rescue squads cannot reach the victims quickly enough. This problem is acute in high risk patients where the likelihood and frequency of cardiac arrest are eminent.

A successful emergency intervention provides prospects of long term solutions to increase the life expectancy of cardiac arrest patients. Specifically in high risk patients where the use of implantable cardioverter defibrillation (ICD) may be cost prohibitive or medically unadvisable, there is a need for a simple, inexpensive and extremely small device which could be implanted in the patients to keep them alive until rescue squads can either defibrillate them or transport them to an emergency room. As is disclosed hereinbelow, the present invention provides such a device.

Yet another situation involving ventricular fibrillation relates to a condition encountered by many patients who survive myocardial infraction (heart attack). Usually, these patients suffer from the onset of ventricular tachycardia. This condition is generally caused by a racing of the bottom chambers of the heart (the ventricles). In sharp contrast with ventricular fibrillation, ventricular tachycardia is not usually fatal but may cause fainting, loss of consciousness and may degrade into a fatal ventricular fibrillation condition. Ventricular tachycardia is therefore a generally non-emergency condition which should nonetheless be treated with prompt therapy.

Traditional prior art discloses devices and methods which utilize timed low voltage pulses to control ventricular tachycardia. For example, U.S. Pat. No. 4,408,606; U.S. Pat. No. 4,398,536; U.S. Pat. No. 4,488,553; U.S. Pat. No. 4,488,554 and U.S. Pat. No. 4,390,021 generally disclose such devices. Further, pacing devices to generate antitachycardia heart rhythms are generally disclosed in U.S. Pat. No. 4,181,133 and U.S. Pat. No. 4,280,502. Further, the use of antitachycardia pacemakers, implantable cardioverter defibrillator (ICD) and a combination thereof is used in the prior art. U.S. Pat. No. 4,830,006 discloses and ICD integrated with an antitachycardia pacing.

While prior art devices to control ventricular tachycardia have proven practicable there is a need to make them cost and space-volume efficient. Specifically, these prior art devices are bulky, expensive and require large size capacitors and batteries to provide the high energy required for defibrillation backup.

Accordingly, there is a need for an economical, efficient and reliable universal device for use in the control and therapy of atrial and ventricular fibrillation and ventricular tachycardia. Particularly, there is a need for a device which is adaptable to various patient conditions involving cardiac arrhythmias. The present invention discloses several devices and methods which are advantageously implemented to meet these and related needs.

SUMMARY OF THE INVENTION

The present invention generally provides an electrical method and device of stimulating cardia cells to affect a partial contraction of the heart to force cardiac output during ventricular fibrillation, hemodynamically compromising tachycardia and/or when a ventricular tachycardia is transformed into a ventricular fibrillation.

The present invention advantageously applies electrical forcing fields to the ventricles such that a cardiac output is obtained on an emergency basis to control arrhythmias or to support life until a more extensive intervention is undertaken. One of the principal objectives of the invention is to maintain a minimum level of ventricular output which may not necessarily be sufficient for defibrillation.

In one of the preferred embodiments, a forcing field is generated by applying approximately 30–200 volts across the ventricles at a rate of approximately 100–180 beats per minute. These electrical fields are applied after detection of a ventricular fibrillation and maintained for up to several hours. This will generate a cardiac output which is a function of the normal maximum capacity. The heart has a four or five times reserve capacity so a function of normal pumping activity will maintain life and consciousness. Various waveforms can be used to optimize the electrical efficiency or patient comfort.

Specifically, one of the preferred embodiments of the present invention includes, inter alia, an electronic system and a lead system for delivering defibrillation shocks to the atrium. It also includes a lead system and electronics for delivering electrical cardiac output forcing pulses to the ventricle thereby providing a safety system in the event the atrial defibrillator shock leads to ventricular fibrillation. In the event ventricular fibrillation is sensed or is eminent, the electrical cardiac output forcing (ECOF) system will force cardiac output for a period of up to several hours thus giving the patient enough time to get to the hospital. This will also enable rescue crews to gain valuable time and perform an external defibrillation therapy as apparent.

Yet another preferred embodiment is tailored for implantation in high risk patients who have never had defibrillation. If the patients do fibrillate later, the ECOF system forces a cardiac output for a period of up to several hours thus giving the patients enough time to get to a hospital. Thereafter, the patients may be equipped with an ICD device. Thus, this embodiment of the present invention lends itself for a single use to force cardiac output over a period of hours until effective long term intervention alternatives could be implemented.

In sharp contrast, an ICD is almost a permanent implant intended to deliver several defibrillation shocks over a period of years. Further, in sharp contrast with an ICD, the ECOF is designed only to temporarily force cardiac output. Further, the ECOF of the present invention is advantageously implantable in high risk cardiac patients without a history of hemodynamically compromising tachycardia or fibrillation.

In yet another embodiment, the present invention provides a method and apparatus to stimulate fibrillating cardiac cells with pulses of appropriate voltage, rate and duration to affect a partial contraction of the heart. In the preferred embodiment, the method and device of the present invention are advantageously implemented as a backup for antitachycardia pacing in the event the pacing process/therapy results in accelerating a ventricular tachycardia to a ventricular fibrillation. The ECOF of the present invention promotes sufficient cardiac output to maintain life and consciousness until advanced intervention therapy could be implemented.

Accordingly, the embodiments disclosed herein indicate some of the various advances of the present invention. These embodiments and the alternatives thereof provide methods and devices with performance efficiency and very high economics in weight, space-volume conservation as well as cost over the prior art. Other features, aspects and advantages of the invention will become apparent upon examination of the following description and drawings dealing with several specific embodiments thereof.

DESCRIPTION OF THE PREFERRED EMBODIMENT

The present invention will now be described more filly hereinafter with reference to the accompanying drawings in which preferred embodiments of the invention are shown. This invention may, however, be embodied in many different forms and should not be construed as limited to the embodiment set forth herein. Rather, applicants provide these embodiments so that this disclosure will be thorough and complete and will convey the scope of the invention to those skilled in the art.

Figure 1:
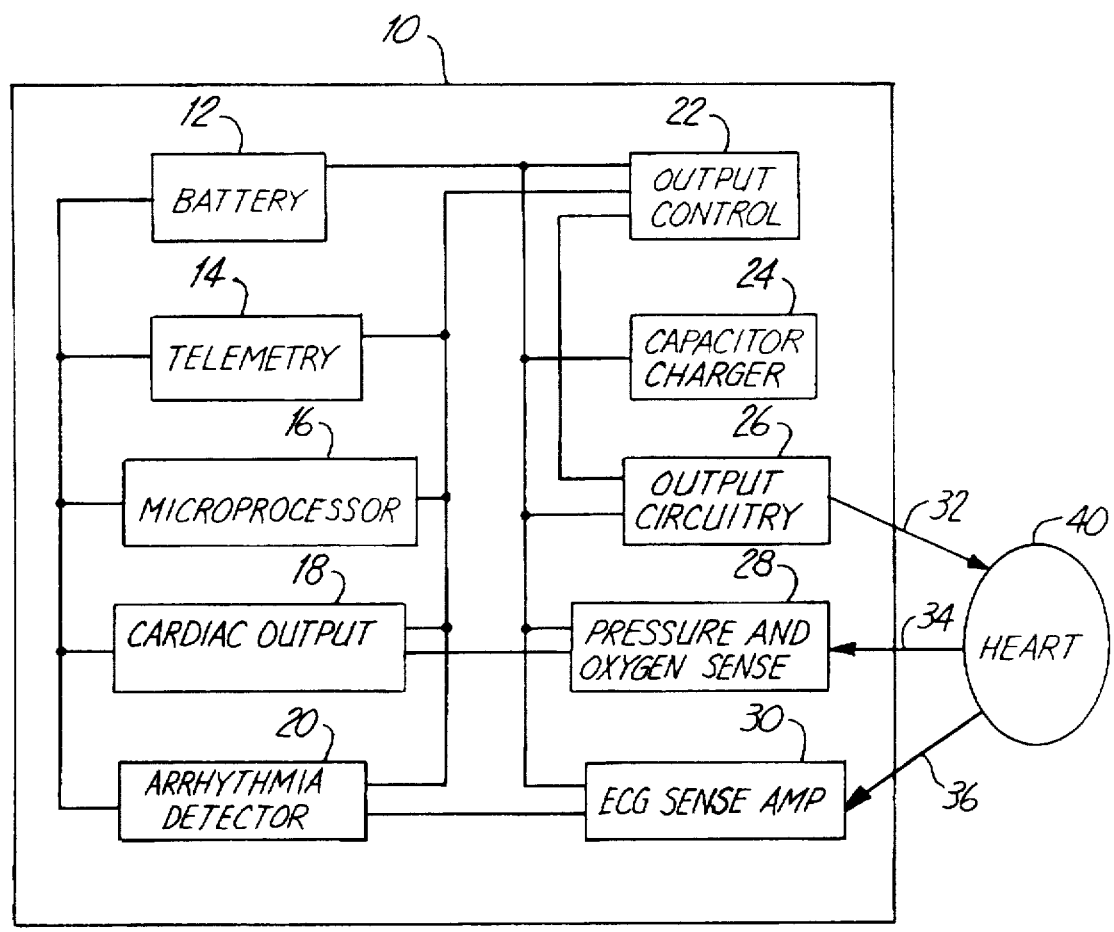
FIG. 1 is a block diagram illustrating a system constructed in accordance with the principles of the present invention.

FIG. 1 is a block diagram illustrating a system 10 constructed in accordance with the principles of the present invention. The device circuitry is connected to the heart 40 via a series of leads: output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example, fibrillation, tachycardia or asystole. The circuit also contains an optional pressure sensing and/or oxygen content sensing section 28 which amplifies and conditions a signal from an optional pressure or $O_2$ sensor from within the heart or artery. The output of the pressure/$O_2$ content sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if Electrical Cardiac Output Forcing (ECOF) is appropriate. If forcing is indicated, the microprocessor 16 prompts the output control 22 to charge a capacitor within the output circuit 26 via the capacitor charger 24. The output control 22 directs the output circuitry 26 to deliver the pulses to the heart 40 via the output leads 32. The microprocessor 16 may communicate with external sources via a telemetry circuit 14 within the device 10. The power for the device 10 is supplied by an internal battery 12.

Figure 2:
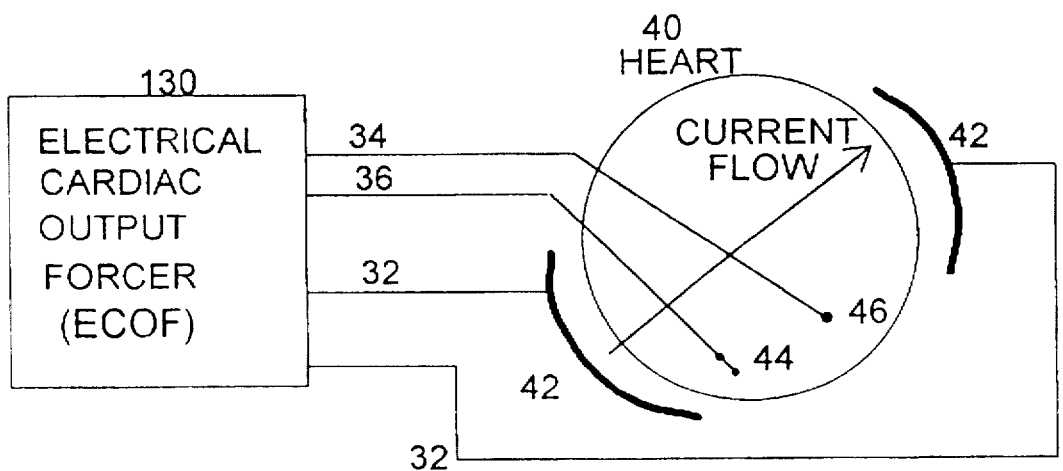
FIG. 2 shows a connection of an implantable embodiment of the device to the heart in an epicardial patch configuration.

FIG. 2 is a diagram showing the connection of the device 130 to the heart 40 in an epicardial patch configuration. In this configuration, current passes through an output lead pair 32 to electrode patches 42 which direct the current through the heart 40. There is an optional pressure sense lead 34 which passes the signal from an optional pressure transducer 46 which lies in the heart 40. The ECG is monitored by sense electrodes 44 and passed to the device 130 by a lead 36. The area of the electrodes 42 is a least 0.5 cm². The size of the electrode is greater than that of a pacing lead and no more than that of a defibrillation electrode or between approximately 0.5 cm² and 20 cm² each.

Figure 3:
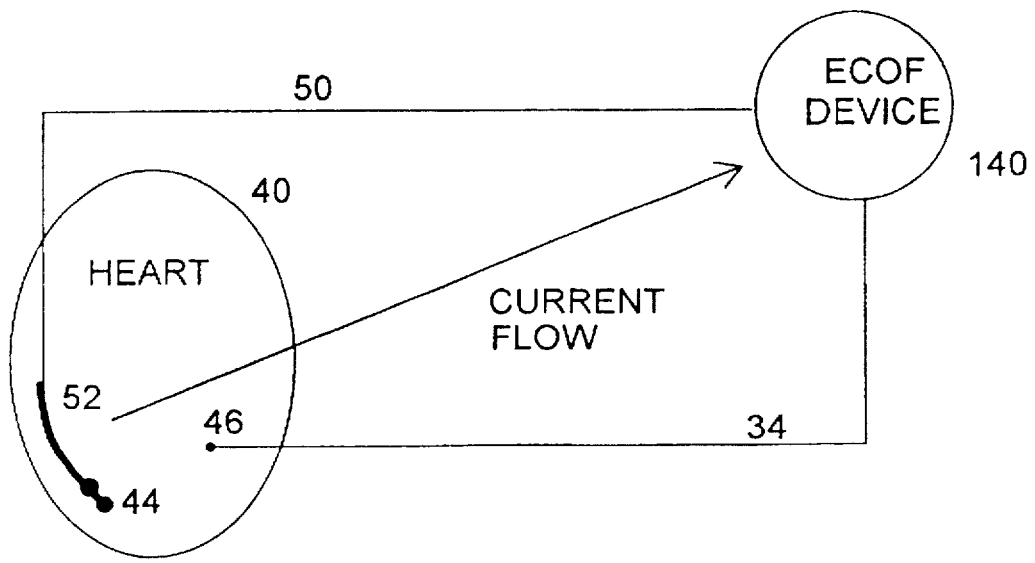
FIG. 3 shows the connection of an implantable embodiment of the device to the heart using an endocardial lead system and the device housing as an electrode.

FIG. 3 shows a non-thoractomy system embodiment of the invention. In this system, the current passes from a coil electrode 52 in the heart 40 to the housing of the device 140. An endocardial lead 50 combines the ECG sensing lead and the pulse output lead. The ECG is monitored by sense electrodes 44 in the heart 40 and passes through the endocardial lead 50. There is an optional pressure transducer or oxygen content sensor 46 in the heart 40 which passes a signal to the device 140 via optional lead 34.

Figure 4:
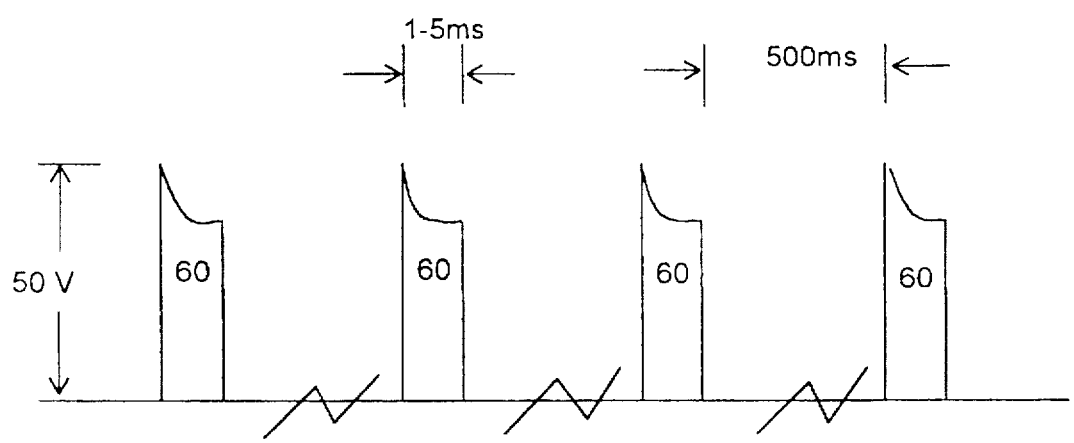
FIG. 4 is a diagram showing a representative pulsatile electrical signal.

A series of forcing pulses 60 are shown in FIG. 4. The pulses are approximately 50 V in amplitude with a spacing of approximately 500 ms. The 50 V and the 500 ms pulse spacing are chosen as illustrative for an implantable embodiment. The forcing pulse interval is chosen to maximize cardiac output within the limits of the device circuitry and the response of the heart muscle. An interval of 500 ms corresponds to a heart rate of 120 beats per minute. This will produce a greater output than a typical resting rate of 60 beats per minute. However, a rate of 240 beats per Lute would produce a lower output due to mechanical limitations of the heart. Thus a practical range is 60 to 200 beats per minute is appropriate. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50 Ω, the power during the pulse is $P=V^2/R=50 V*50 V/50 Ω=50 W$. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes. (10,000 J/4.8 W =2083 seconds). Thirty five minutes may not be enough time to transport the patient to a hospital. Therefore 200 V represents the highest practical voltage for continuous operation in an implantable embodiment, although voltages of up to 350 V (maximum voltage for electrolytic capacitor) could be used for short periods and adjusted down when hemodynamic output is verified. A practical lower limit is about 10 V. During normal sinus rhythm, 10 V delivered through the patches would pace. However, during fibrillation the 10 V could not pace and only cells very near the electrodes would be captured. This would be insufficient for forcing cardiac output. A typical range would be 30–200 V.

These calculations also suggest other differences between an implantable ECOF and an ICD. With a battery storing 10,000 J and an ECOF pulse having 0.1 J, this ECOF would be capable of delivering 100,000 pulses. An ICD can only deliver 200–400 shocks of about 30 J. The ECOF is also very different from an implantable pacemaker which typically delivers 150,000,000 pacing pulses (5 years at 60 BPM) each of about 0.00005 J.

Figure 5:
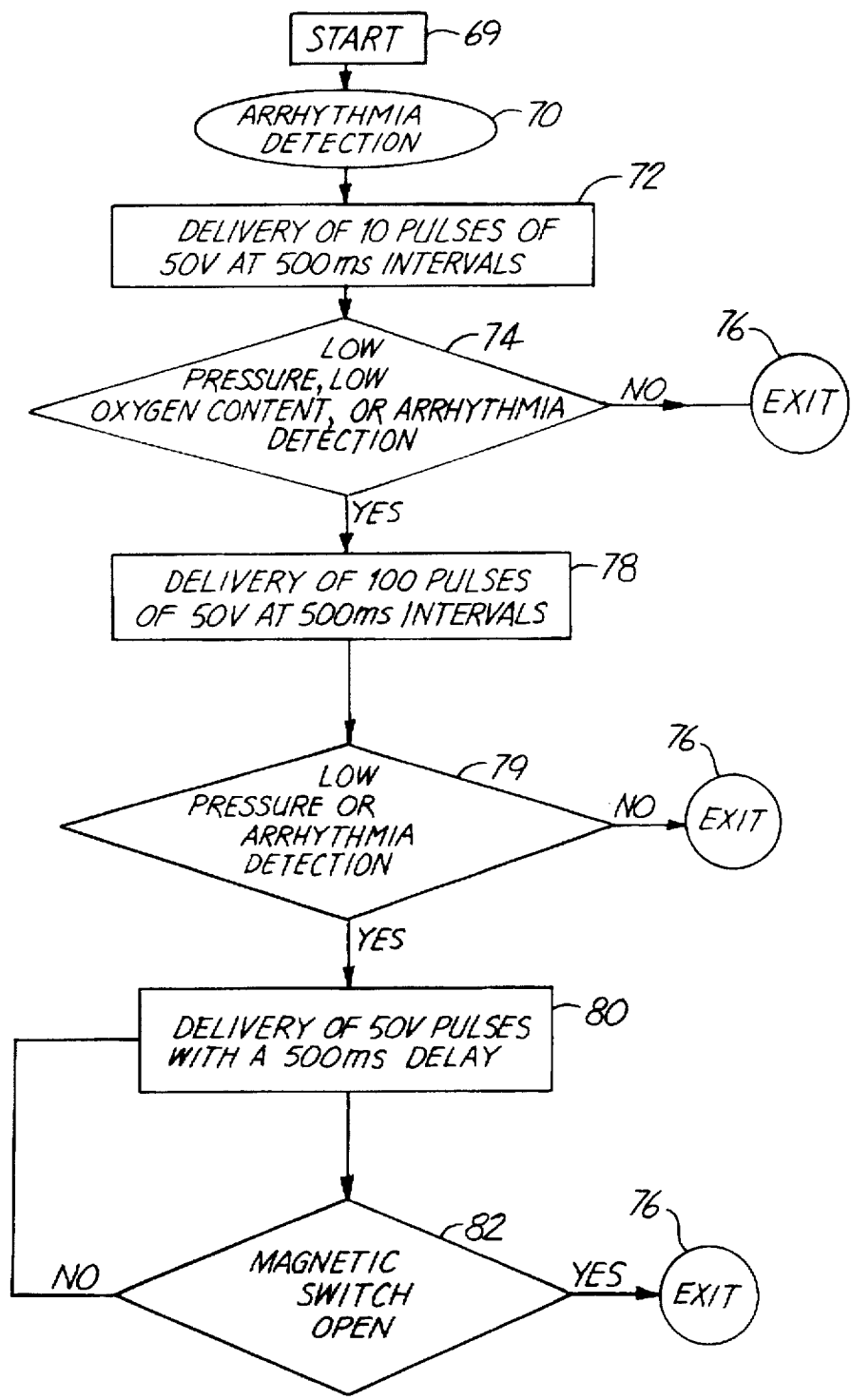
FIG. 5 is a flowchart illustrating one embodiment of the method of the invention.

FIG. 5 is a flowchart illustrating the method of the invention, which is provided for purposes of illustration only. One skilled in the art will recognize from the discussion that alternative embodiments may be employed without departing from the principles of the invention. The flow diagram shown in FIG. 5 represents a method of automatically treating a heart which is in fibrillation, tachycardia, or asystole and thereby pumping inefficiently or not at all. Electrodes are attached 69. A diagnosis of the presence of an arrhythmia is made 70. A series of cardiac output forcing electric pulses 72 is automatically delivered. It should be understood that the therapy 72 may be delivered for any output compromising cardiac arrhythmia. After delivery of 10 forcing pulses (at a rate of 60–200 BPM) in the first block 72, the status of the heart is determined 74. If an arrhythmia is still present and there exists low pressure or low $O_2$ within the heart, more forcing pulses are delivered 78. In step 78 the amplitude of the electrical variable based on the optional blood pressure or oxygen content monitoring means. If the heart is pumping at a safe level, the therapy ceases and exits 76. Note that this means that the ECOF successfully defibrillated the patient's heart even though this is not a primary goal of the system. This could be tested in patients who were scheduled to receive an ICD, in a hospital setting. Those patients who are defibrillated by ECOF pulse therapy could then receive the ECOF instead of the larger ICD. After the therapy 78 has been delivered, the pressure, $O_2$ content and ECG are again monitored 79. If the therapy 78 is successful, it ceases and exits 76. If the therapy 78 is unsuccessful in producing a safe level of pumping efficiency, the method proceeds to a continuous cardiac assist mode 80. The therapy may only be stopped by an external command, for example, a telemetry signal or a magnet which is applied to the chest activating a magnetic reed switch 82 which terminates the therapy and exits 76. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 6:
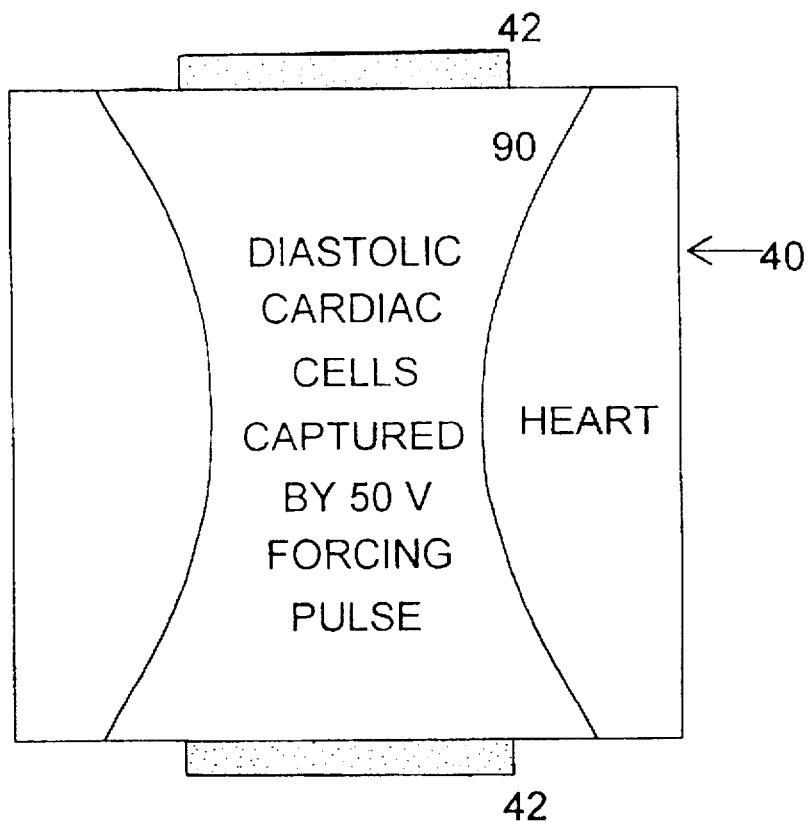
FIG. 6 is a diagram showing the expected effect of a 50 V pulse on the heart during diastole

FIG. 6 is a diagram showing the effect of a 50 V forcing pulse on the heart 40 during electrical diastole (cells at rest). The current is passed through the heart 40 by the electrodes 42. Approximately 60% of cardiac cells 90 would be captured by a 50 V pulse if the cells were in diastole. The captured cells 90 mostly lie in the direct path between the electrodes 42 and near the electrodes 42 where the field strengths are highest. Of course, over a time period of about 100 ms these directly captured cells then propagate an activation wavefront to stimulate the rest of the heart. This so called far-field pacing is not wholly relevant here as the hearts, of interest, are in fibrillation and not in diastole.

Figure 7:
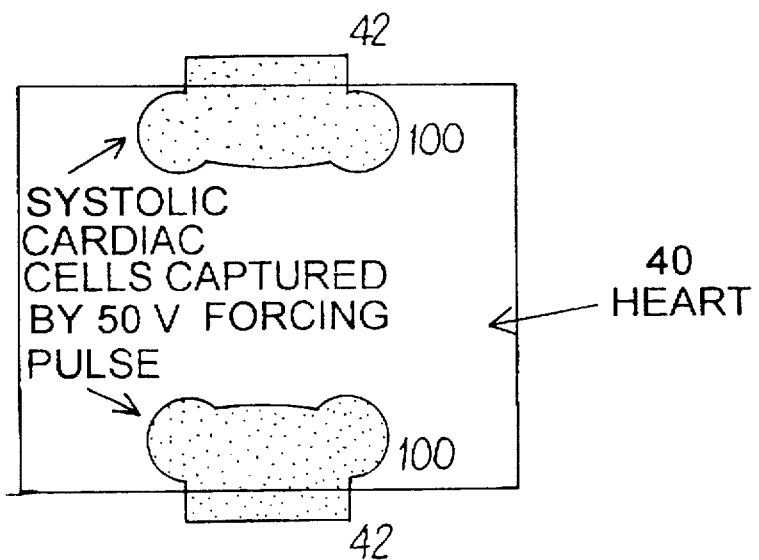
FIG. 7 is a diagram showing the expected effect of a 50 V pulse on the heart during systole.

FIG. 7 is a diagram showing the effect of a 50 V forcing pulse on the heart during electrical systole (cells already stimulated). The current is passed through the heart 40 by the electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (5 V/cm) than those required for diastolic cell capture (0.5 V/cm).

Figure 8:
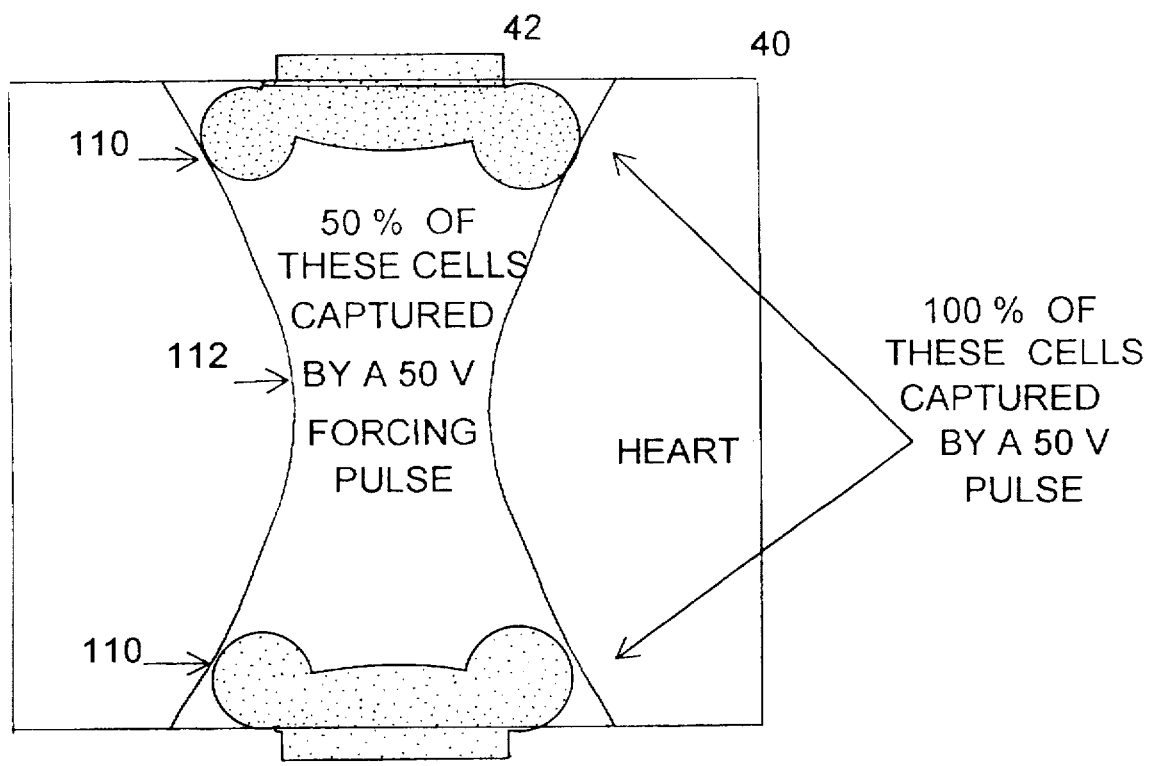
FIG. 8 is a diagram showing the expected effect of a 50 V pulse on the heart during fibrillation.

FIG. 8 is a diagram showing the effect of a 50 V forcing pulse on the heart during fibrillation. During fibrillation there are always cells in systole and diastole simultaneously. But, the vast majority are in systole. The diagram assumes 50% of the cells are in diastole which applies only after several capturing pulses. The current is passed through the heart 40 by the electrodes 42. 100% of the cells 110 nearest the electrodes 42 would be captured due to the high field strength. As shown in FIG. 7, even systolic cells are captured by high field strengths. 50% of the cells 112 in the direct path between the electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the resulting mechanical action and the contribution to cardiac output forcing.

Considering the cardiac cells that are originally in diastole (rows A&B in the table below), the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next consider the activity of the systolic cells (rows C&D). If 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result (Rows A, B, C, and D) is a gain in contraction which forces cardiac output.

The net result over a 200 ms mechanical response is given in the next table. The major contribution is in row (B) from the captured diastolic cells contracting.

| Original Status of the Cells | Percentage of the Cardiac Cells | Status of the Cardiac Cells | Percentage of the Original Status | Percentage of the Total Cells | Mechanical Action | Forcing Cardiac Output Effect |
| --- | --- | --- | --- | --- | --- | --- |
| (A) Diastolic | 50% | Diastolic non-captured | 40% of 50% | 20% | will start to contract on own | positive (+) |
| (B) Diastolic | | Diastolic captured | 60% of 50% | 30% | contract | positive (++) |
| (C) Systolic | 50% | Systolic non-captured | 80% of 50% relax on own | 40% | will start to | negative (−) |
| (D) Systolic | | Systolic | 20% of 50% captured | 10% | hold | neutral (0) |
| TOTAL | 100% | | 100% | 100% | more contraction | positive (+) |

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field. |
| C | Systolic non-captured | -5% | Negative. Cells begin to relax on own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4–5 times reserve capacity.

Figure 9A:
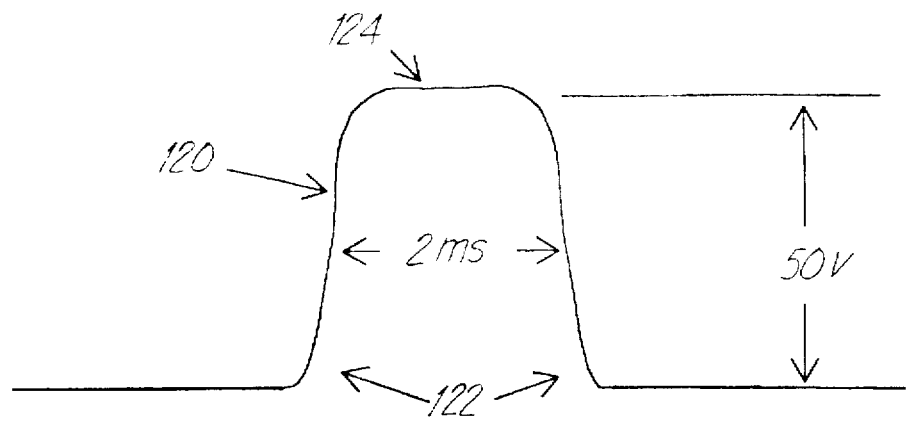
FIG. 9a and FIG. 9b show various waveforms useful for the electrical cardiac output forcing method and apparatus.

FIG. 9 depicts examples of waveforms designed to minimize the twitching of the chest muscles which can be very uncomfortable to the patient. In FIG. 9a is seen a low harmonic pulse waveform 120 which has a very gradual "foot" 122 and a gradual peak 124. Such a pulse has less high frequency energy components and thus is less likely to stimulate the skeletal muscle.

Figure 9B:
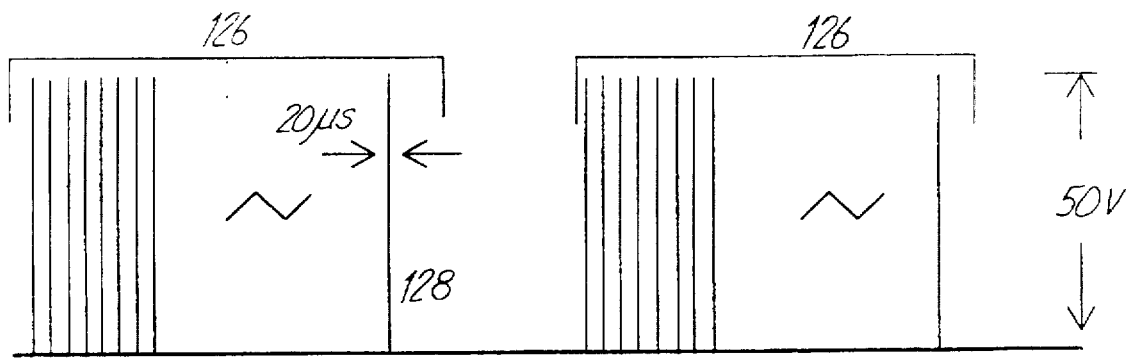

FIG. 9b shows a technique of going to the opposite extreme. Here, each compound forcing pulse 126 is actually composed of 50 very short spikes 128 each of which is 20 μs in width with a 20 μs spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to charge the capacitor to 300 V for the first pulse to capture many cells therefore putting those cells into diastole after a delay of 100–200 ms. At this point the voltage could be lowered to 100 V and pulses delivered every 100 ms. A 3 watt DC-DC converter with a 67% efficiency could provide 100 ms interval forcing pulses assuming a 50 Ω resistance and 1 ms pulse (0.2 J). This rate is too fast for forcing cardiac output due to mechanical limitations, but is very effective for electrical capture. After sufficient capture, the rate of forcing pulses could be slowed down to 100–170 beats per minute for optimum cardiac output.

Figure 10:
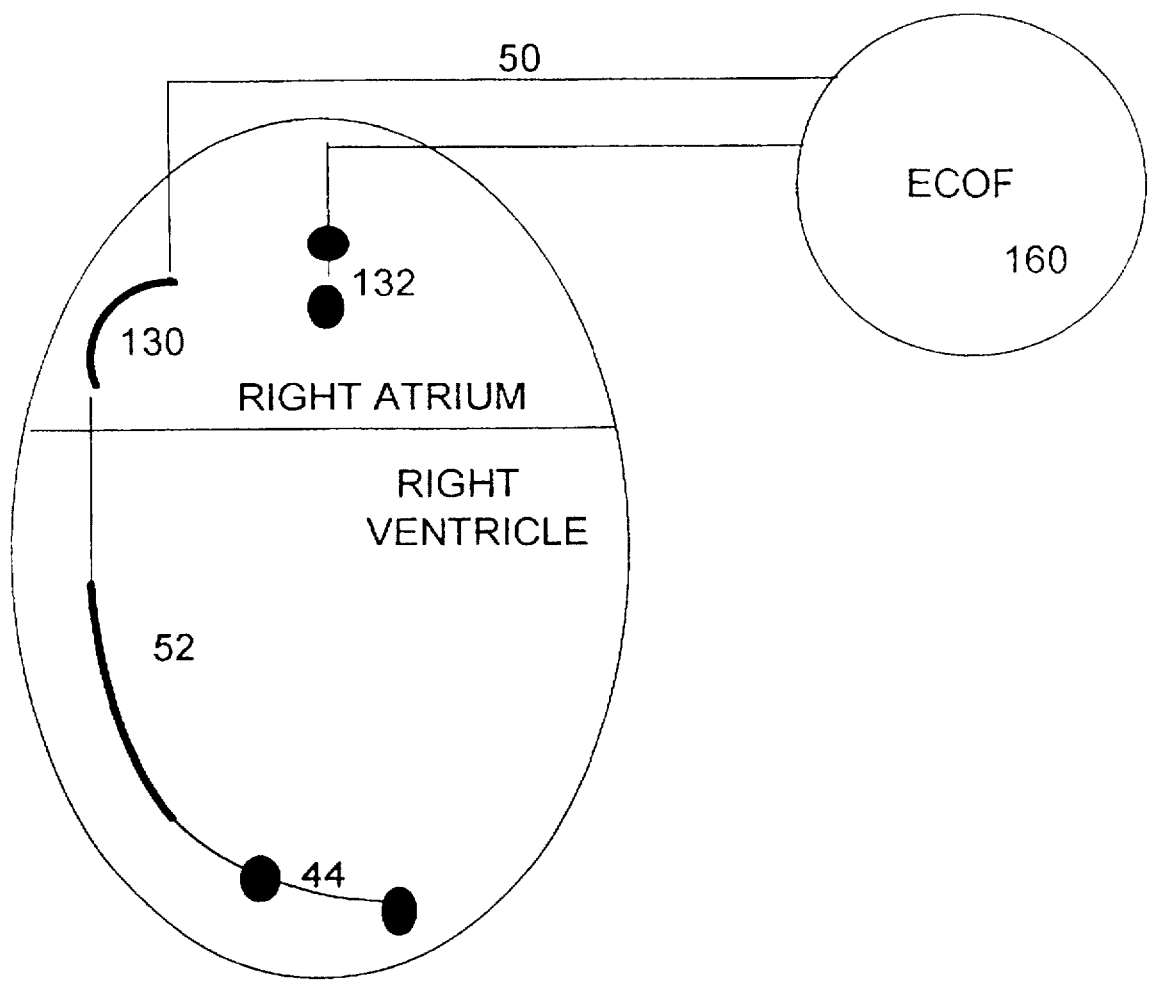
FIG. 10 shows an embodiment which includes separate atrial and ventricular coil electrodes.

The invention may also have a right atrial coil electrode 130 as shown in FIG. 10. If the atria are also in a tachyarrhythmia (assuming that the ventricles are), the right atrial coil delivers a current pulse at a fixed interval prior to the main ventricular pulse delivered by right ventricular coil 52. By synchronizing the ventricular forcers thusly, the output of the atria is employed which can increase total cardiac output by at much as 20%.

Figure 11:
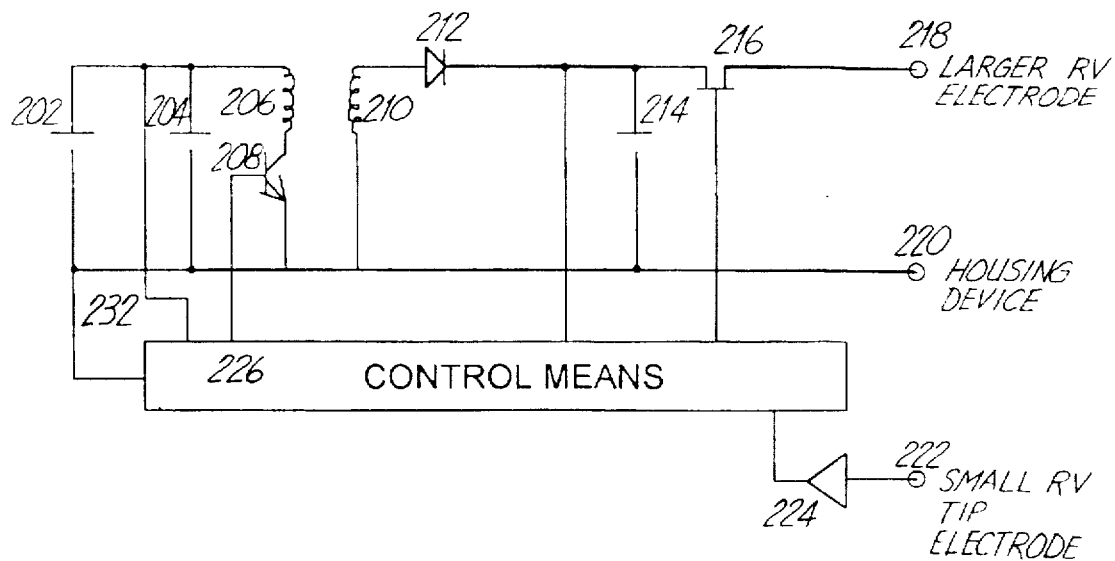
FIG. 11 is a schematic of the basic ECOF system.

FIG. 11 shows a basic schematic of the system. A high capacity implantable grade battery 202 is used to power the overall system. This battery could be of any high capacity lower impedance type of implantable cell. This would include lithium silver vanadium oxide, thionyl chloride, or titanium carbon monofluoride for example. Various cells have different advantages. The lithium silver vanadium oxide cells have extremely powerful outputs but rather limited energy densities. The titanium carbon monofluoride cells have a lower power output but have twice the energy density of the lithium silver vanadium oxide cell. The cell (or battery of cells) need be capable of providing at least 100 mW to deliver pulses of sufficient voltage and rate to temporarily maintain cardiac output.

The output voltage from the cell is smoothed by small capacitor 204. The power from the cell 202 is then used to deliver a current through flyback transformer primary winding 206. That current is generated on an interrupted basis through winding 206 by the operation of switching transistor 208 which is controlled by control means 226. The output energy from the flyback transformer is directed through secondary winding 210 and passes through diode 212 and is stored in capacitor 214.

A typical specification for capacitor 214 is 60 μF and 70 V. The time constant with a load of 100 Ω and the 60 μF (microfarads) capacitor is 6 ms (milliseconds) which is truncated to produce a reasonably level 3 ms wide forcing pulse. Capacitors as small as 10 μF would also work although they would deliver a higher voltage and more narrow pulse while capacitors with values of 200 μF would also be usable. In the case of the 60 μF capacitor and a maximum output voltage of 70 V the energy can be calculated by the formula $E=½ C V^2$ giving a total energy of 0.15 J. This is an extremely small capacitor compared to the typical 30–40 J capacitor which is the total capacitive storage in an ICD. Even if the ECOF was designed to operate to voltages of 200 volts which are immensely practical then the total energy storage of the capacitor would only be 1.2 J. With the rule of thumb that high density aluminum electrolytic capacitors are capable of storing about 1 J per $cm^3$ the capacitor would have a total volume of only about 1 $cm^3$. This is in sharp contrast to the very large capacitors of present ICDs which are on the order 20 $cm^3$. This is one of the reasons why the ECOF can be made much smaller than the an ICD.

Pulses are delivered to the heart from the energy stored in capacitor 214 by the operation of output switch 216 which is controlled by control means 226. Those pulses are then delivered to an electrode in or near the heart which is typically a large right ventricular coil which is connected to terminal 218. The other pole for the heart current would typically be the device housing itself connected to terminal 220. The fibrillation of the heart is detected by the use of a small right ventricular tip electrode connected to terminal 222 whose signal is then amplified by amplifier 224 and then fed into the control means. This amplifier is capable of recognizing ventricular fibrillation or a high rate ventricular tachycardia and thus initiating, through the control means, the electrical cardiac output forcing. The battery voltage is monitored through connection 232 by the control means. This allows the control means to be aware of the state of the battery charge. The control means can thus signal for a change in the device or switch to a more efficient waveform with a decreased voltage on the battery.

Figure 12:
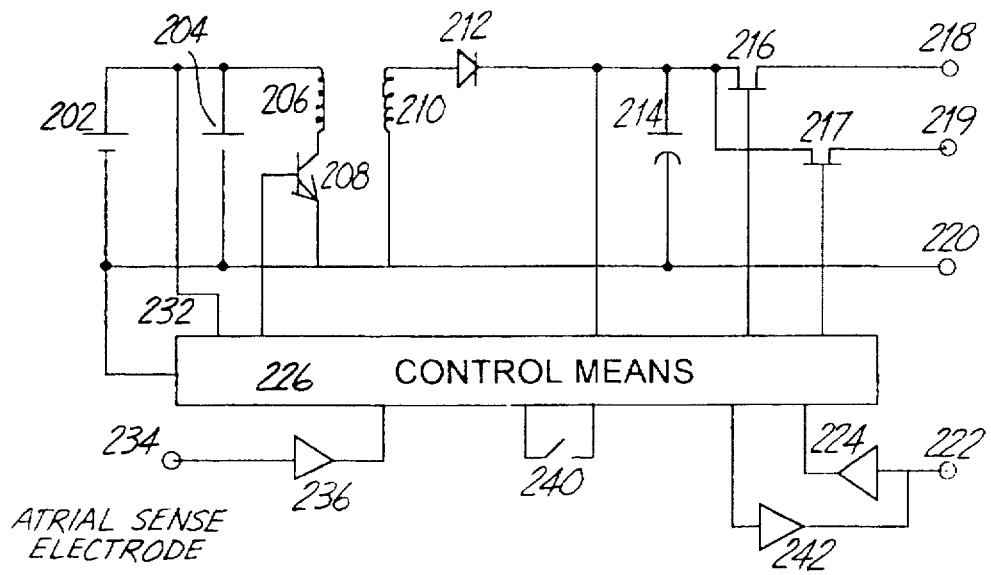
FIG. 12 is a schematic of a more complex version of the ECOF device.

FIG. 12 shows a more complicated embodiment of the system.

Connection 234 goes to a sense electrode in the atrium. This signal is then run through amplifier 236 and then to the control means. The sensing of the atrial signal is useful for a number of reasons. One reason is that by monitoring the electrogram from both the ventricle and the atrium, the control means can make a more intelligent decision about the presence or absence of a ventricular fibrillation or ventricular tachycardia. Secondly, the atria are responsible for about 20% of the cardiac output. By sensing the atrial contraction, and synchronizing to that, the ECOF should be able to increase its output efficiency. The lead in the right atrium could also provide ECOF pulses prior to ventricular ECOF pulses, if the atrial are also fibrillating. This would increase cardiac output even more. The atrial coil is connected to terminal 219 and connected to switch 217 and controlled by control means 226.

Magnetic reed switch 240 allows a patient or physician to terminate the (possibly uncomfortable), ECOF pulsing by placing a strong magnet over the chest. That magnetic field is detected by the magnetic switch 240 which then inhibits the electrical output. Alternatively the sensor could be a Hall effect or MAGFET magnetic sensor.

Output amplifier 242 is used to generate pacing pulses on the order of the battery voltages. These pulses have an amplitude of typically less than 10 V. They are delivered to the heart through the same electrode which is connected to node 222. This feature is necessary to those high-risk patients which are also suffering from a bradycardia. Since the ECOF device is closer in size to a conventional bradycardia pacemaker, the physician can easily implant it in pacing patients and gain the lifesaving benefits of ECOF in the event of a cardiac arrest.

Figure 13:
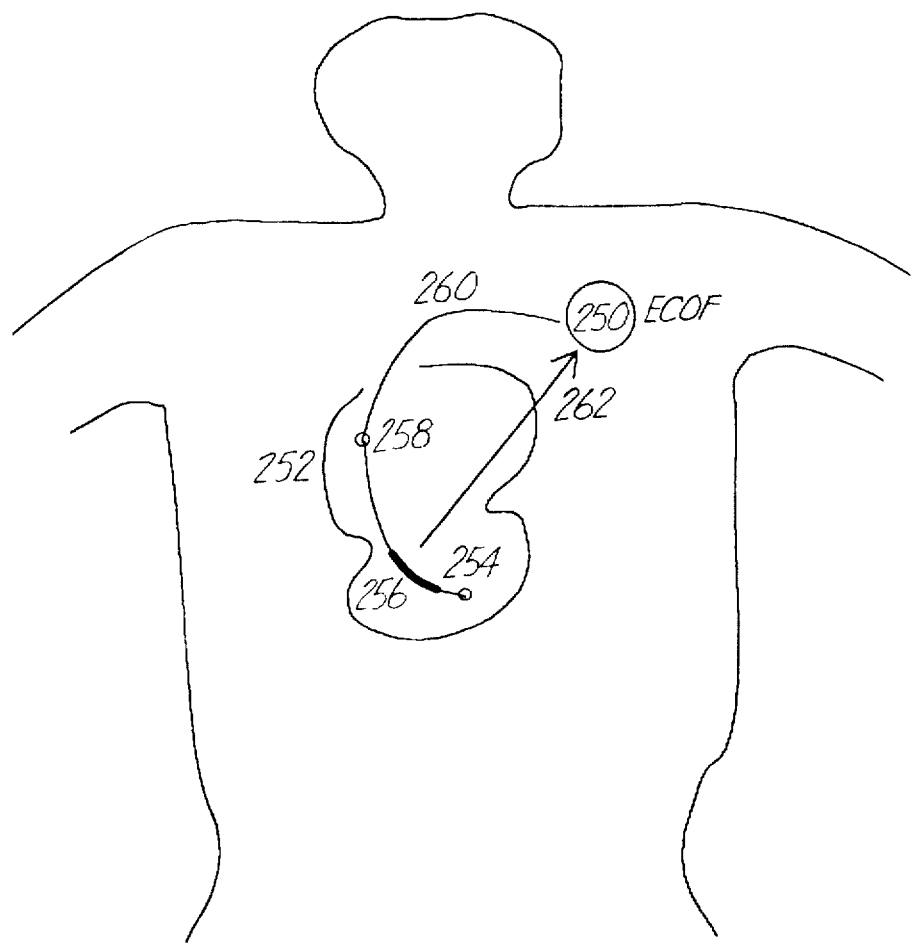
FIG. 13 shows the ECOF implanted in the human body along with its lead system.

FIG. 13 shows the ECOF 250 implanted in a left pectoral region of the patient. Lead 260 is then run through a vein and down into the right atrium and right ventricle of the heart. The right ventricular tip electrode 254 is used to sense the electrical activity to diagnose fibrillation and is connected to terminal 222 (in FIG. 11). A larger coil electrode 256 is connected to terminal 218 (in FIG. 11) and is used to deliver the moderate voltage pulse which will drive current from this coil 256 along a path 262 through the majority of the ventricle and towards the ECOF device 250.

Finally, an atrial sensing lead 258 lies in the atrium to sense the atrial electrogram to aid in diagnosis or synchronizing of the ECOF output.

Figure 14:
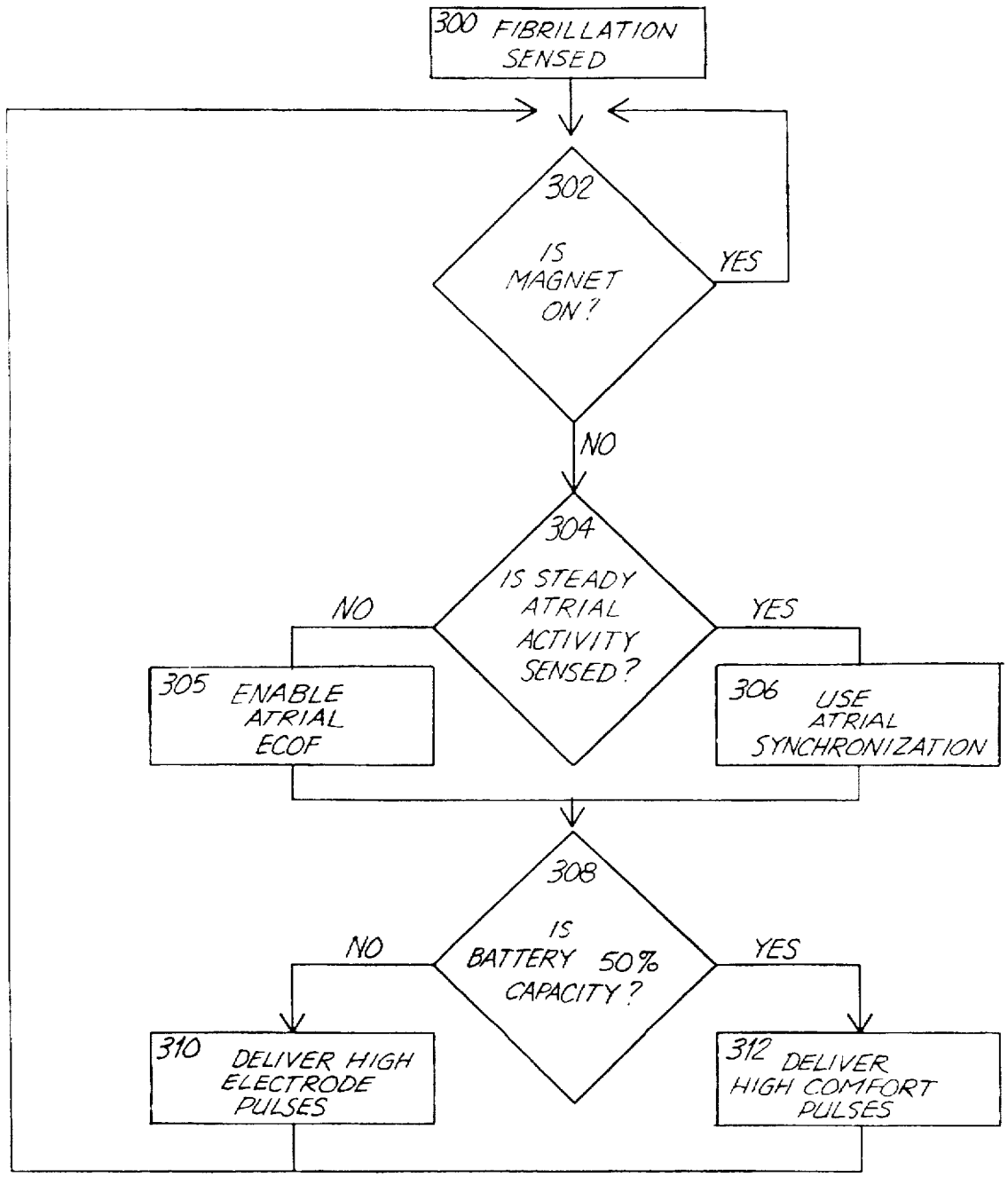
FIG. 14 shows a flow chart of the method of use of the ECOF device.

FIG. 14 depicts the operational sequence for the ECOF device optimized for high-risk cardiac patients. The first step in the method is the sensing of fibrillation 300. After fibrillation is sensed, then the decision 302 is made as to whether or not the magnet is present. If it is, then the device simply waits and performs no additional therapy until the magnet is removed. In the absence of the magnet then the procedure proceeds down and an attempt is made to sense atrial activity on a steady basis 304. If this is successful, then the decision is made to use atrial synchronization as shown in box 306. Otherwise atrial ECOF therapy is enabled 305. Step 308 tests the battery capacity. If the battery is still in the early stages of its life, then the ECOF device delivers high-comfort pulses 312 to the ventricle. These pulses are shaped to minimize the high-frequency edges which are typically found in electrical stimulation therapy. Unfortunately these low-spectral content high-comfort pulses are relatively inefficient as much energy must be lost in the output switches such as switch 216 (in FIG. 11) in order to shape these output pulses. After the battery has lost half its capacity the unit will automatically shift over towards the delivery of high-efficiency pulses which is step 310.

Figure 15A:
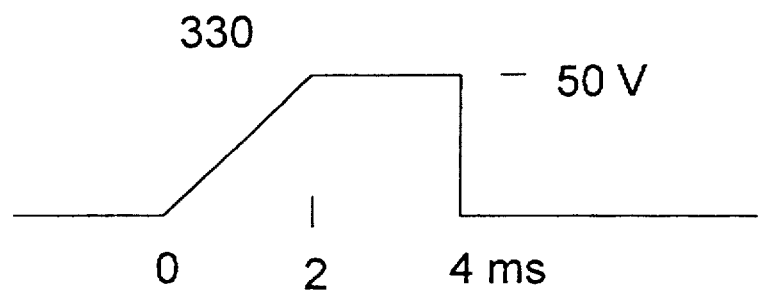
FIG. 15 shows a sample of the output waveforms.
Figure 15B:
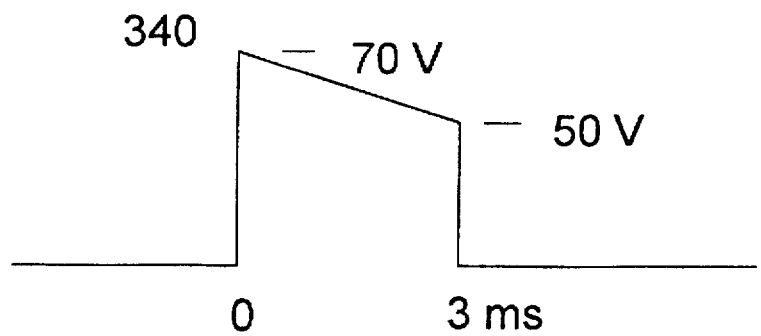

FIG. 15 depicts two very practical sample pulses which the ECOF device could use. Waveform 330 is a high comfort pulse. The waveform begins at 0 volts and gradually climbs to 50 V over a 2 ms period of time. This represents a very gradual voltage change of only 25 V per ms. The pulse then maintains the 50 V for a period of an additional 2 ms. This slow rise time on the leading edge makes the pulse much less irritating to the patient and much less likely to stimulate skeletal muscles and nerves. This is generated by slowly turning on output transistor 216 in FIG. 11. Alternatively, the waveforms in FIG. 9 could be generated although the control is more complex.

The high efficiency pulse 340 is designed to capture all of the energy from the capacitor without any waste. It thus rises nearly instantaneously to 70 V and tapers to 50 V during the 3 ms width of the pulse then finally returns to 0 V. This is a very efficient pulse in that there are no losses from the switches being used for shaping. It is also a relatively uncomfortable pulse in that the high spectral content of the sharp leading edge tends to stimulate nerves and skeletal muscles in the patient. High comfort stimulation wave forms are taught by Mehra in U.S. Pat. No. 5,0818,522 for an external pacing apparatus.

It should be understood that various alternatives to the embodiments of the invention described herein may be employed in practicing the invention. It is intended that the following claims define the scope of the invention and that structures and methods within the scope of these claims and their equivalents be covered thereby.

We claim:

1. An implantable device for maintaining cardiac output of a patient's heart during tachyarrhythmia wherein electrical forcing fields in the form of electrical pulses are applied to the heart until the onset of the tachyarrhythmia is eliminated, the device comprising:

a power supply system including a rechargeable battery;

means for detecting arrhythmia connected to said power supply system;

interface means for adapting to connect said power supply system and said means for detecting arrhythmia to the patient's heart; and means for controlling electrical output connected to said means for detecting arrhythmia, said power supply system and said interface means to thereby deliver multiple electrical pulses to the heart after detection of said tachyarrhythmia, wherein said electrical pulses include a voltage between 30 and 200 volts, to induce suboptimal contraction in the patient's heart and force a minimum level of cardiac output sufficient to maintain life.

2. The device of claim 1 in which said electrical pulses are delivered at a rate between 60 and 200 pulses per minute.

3. The device of claim 1 in which the arrhythmia is of an asystole type relating to absence of cardiac contraction and leading to cardiac arrest.

4. The device of claim 1 further comprising means for monitoring blood pressure wherein said means for monitoring includes operable connections and communication with said means for detecting arrhythmia.

5. The device of claim 4 wherein said means for monitoring blood pressure further monitors cardiac output and also includes means for adjusting amplitudes of said electrical pulses in cooperation with said means for controlling output to maintain a predetermined level of cardiac output, thereby conserving electrical energy.

6. The device of claim 5 wherein said means for monitoring blood oxygen content further includes means for adjusting amplitudes of said electrical pulses in cooperation with said means for controlling output to maintain predetermined level of cardiac output, thereby conserving electrical energy.

7. The device of claim 1 further comprising means for monitoring blood oxygen content incorporated therein to provide a level of oxygen measurement as part of an overall assessment of the patient's condition.

8. The device of claim 1 wherein each of said electrical pulses includes rounded profile edges with no sharp transitional rises, thereby minimizing patient discomfort and chest twitching.

9. The device of claim 1 wherein each of said electrical pulses includes a patterned train of at least 10 narrow pulses, structured to minimize patient discomfort and chest twitching.

10. The device of claim 1 in which said means for detecting arrhythmia includes means for reassessing the presence of arrhythmia, at predetermined intervals, and said interface means cooperates with said output control means to stop said electrical current pulses if the arrhythmia is no longer detected.

11. The device of claim 1 further comprising means for synchronizing ventricular electrical pulses with atrial depolarizations.

12. The device of claim 1 further comprising separate coil electrodes adapted to be placed in the right atrium and the right ventricle of the patient's heart and the coil electrode in the atrium delivers an electrical pulse between 100 and 300 ms earlier than the delivery of pulses to the right ventricular pulse.

13. The device of claim 12 further comprising means to independently vary electrical current amplitudes of said atrial and ventricular electrodes.

14. The device of claim 1 wherein said means for controlling output includes a capacity to deliver said electrical current pulses for at least one hour to maintain cardiac output.

15. A method for electrically forcing cardiac output at substantial defibrillation level during an arrhythmia, comprising the steps of:

detecting the presence of the arrhythmia in a human heart; and delivering electrical pulses to said human heart, wherein said electrical current pulses are delivered at a rate of between 60 and 200 pulses per minute, and said electrical current pulses are strong enough to force suboptimal contraction in parts of the patient's heart, thereby providing a level of cardiac output sufficient to maintain life without optimally defibrillating the patient.

16. The method of claim 15 wherein said step of delivering electrical pulses is repeated for at least one hour to maintain cardiac output.

17. A cardiac pacemaker comprising:

a battery;

arrhythmia detection circuitry connected to said battery;

a voltage inverter connected to the battery to increase the voltage to a level of between 30 and 200 volts; and output circuitry, controlled by the arrhythmia detection circuitry connecting the voltage inverter to a patient's heart to deliver the inverter voltage repetitively in order to directly force a suboptimal contraction in the patient's heart to maintain a minimum level of cardiac output in the event of an arrhythmia.

18. The pacemaker of claim 17 wherein the repetitive inverter voltage is delivered at a rate between 60 and 200 pulses per minute.

19. The pacemaker of claim 17 wherein the output circuitry turns on gradually and thus provides at least one gradually rising pulse profile with a rounded edge.

20. The pacemaker of claim 17 wherein the output circuitry turns on gradually and thus provides a gently sloped leading edge profile.

21. The pacemaker of claim 17 further comprising means to detect atrial contraction and means to synchronize said output circuitry to the atrial contraction.

22. The pacemaker of claim 17 wherein the battery means has sufficient storage to provide the forcing pulses for at least one hour.

23. The pacemaker of claim 17 wherein the inverter output voltage is adjusted down to maintain cardiac output while minimizing patient discomfort and the battery life.

* * * * *